United States Patent [19]

Iwata et al.

[11] Patent Number: 4,557,154
[45] Date of Patent: Dec. 10, 1985

[54] SHOCK ABSORBING MECHANISM IN AUTOMATIC ANALYZING AND MEASURING APPARATUS

[75] Inventors: Toyotaro Iwata; Kunio Nakajima; Hiroyuki Otsuki, all of Hyogo, Japan

[73] Assignee: Toa Medical Electronic Co., Ltd., Hyogo, Japan

[21] Appl. No.: 418,654

[22] Filed: Sep. 16, 1982

[30] Foreign Application Priority Data

Sep. 18, 1981 [JP] Japan ................... 56-147166

[51] Int. Cl.$^4$ ............... F16H 27/02; F16D 7/06; G01N 35/00
[52] U.S. Cl. ................... 74/89.21; 192/56 R; 422/65; 464/36
[58] Field of Search .............. 192/56 R, 150; 74/89.21, 89.22; 464/36; 422/65

[56] References Cited

U.S. PATENT DOCUMENTS

| | | | |
|---|---|---|---|
| 2,773,370 | 12/1956 | Intraub et al. | 192/56 X |
| 3,095,955 | 7/1963 | Orwin | 192/56 R |
| 3,143,393 | 8/1964 | De Seguin Des Hons | 23/253 |
| 3,185,275 | 5/1965 | Orwin | 192/56 R |
| 3,282,387 | 11/1966 | Becker et al. | 192/56 R X |
| 3,616,705 | 11/1971 | Platz | 74/89.22 |
| 3,842,680 | 10/1974 | Vollick et al. | 73/425.4 P |
| 3,881,369 | 5/1975 | Looney | 74/89.22 X |
| 3,994,587 | 11/1976 | Yamamoto et al. | 356/73 |
| 4,007,818 | 2/1977 | Orwin | 192/56 R |
| 4,076,503 | 2/1978 | Atwood et al. | 23/259 |
| 4,204,767 | 5/1980 | Kato et al. | 356/444 |
| 4,281,557 | 8/1981 | Ohta et al. | 74/89.22 |
| 4,286,441 | 9/1981 | Scheneman et al. | 192/56 R X |
| 4,299,796 | 11/1981 | Esch | 422/63 |
| 4,332,472 | 6/1982 | Kato et al. | 356/344 |
| 4,338,279 | 7/1982 | Orimo et al. | 422/64 |
| 4,495,149 | 1/1985 | Iwata et al. | 422/65 |

OTHER PUBLICATIONS

GIB Precision Limited's Brochure Titled "The Autogard Family of Torque Limiters".
IBM Technical Disclosure Bulletin, vol. 18, No. 11, Apr. 1976, "Telescoping Spectrophotometer Dip Probe".

Primary Examiner—Rodney H. Bonck
Attorney, Agent, or Firm—Pearne, Gordon, Sessions, McCoy, Granger & Tilberry

[57] ABSTRACT

A shock absorbing mechanism, comprising a slip clutch, is interposed between drive sources and a body carrying optical and dispensing means in an automatic analyzing and measuring apparatus which repeatedly moves and stops said body in a plane to dispense reagents and samples at specified positions in the plane and to optically scan changes in the samples after reacting with the reagents.

2 Claims, 2 Drawing Figures

SHOCK ABSORBING MECHANISM IN AUTOMATIC ANALYZING AND MEASURING APPARATUS

BACKGROUND OF THE INVENTION

This invention relates to a mechanical shock absorbing mechanism in an automatic analyzing and measuring apparatus.

In recent years an automatic analyzing and measuring apparatus has been developed for applying predetermined quantities of reagents and samples to a multiplicity of reaction carriers arrayed in two dimensions, allowing each component contained in a sample to react with a reagent to provide a reaction product which changes color and forms precipitates, and optically detecting the reaction product by an optical scanning device, whereby a multiplicity of the reaction products on the reaction carrier can be submitted to qualitative and quantitative determination in continuous fashion. Since a dispensing mechanism and/or the scanning device in the above-mentioned apparatus must be accurately transported in a plane along X and Y axes, it is important to design the apparatus in such a manner that these movable components will not interfere with each other's operation, or inadvertently contact each other, when they are started and stopped. Such apparatus is the subject of our copending application Ser. No. 419,038, filed Sept. 16, 1982, now U.S. Pat. No. 4,495,149.

Problems remain, however, in that excessive forces can be produced between these movable components and the sources for driving them when the dispensing mechanism and/or optical scanning device is accidentally contacted by the operator or brought into contact with an item of peripheral equipment, or when the apparatus malfunctions or is subjected to an abrupt correction operation by a handling error. These excessive forces can impede the continuous operation of the apparatus and necessitate the replacement of parts.

SUMMARY OF THE INVENTION

Accordingly, an object of the present invention is to provide means for dealing with troubles in the mechanical operation of an automatic analyzing and measuring apparatus of the aforementioned type.

Another object of the present invention is to provide a shock absorbing mechanism for use in an automatic analyzing and measuring apparatus, wherein the power transmission path from driving units to movable components such as an optics/dispensing mechanism is safely interrupted to isolate the driving units from the movable components and then allow resumption of the continuous analytical measurements when conditions return to normal.

According to the present invention, these and other objects are attained by providing a shock absorbing mechanism in an automatic analyzing and measuring apparatus of the type which includes an optics/dispensing device and an X-Y drive mechanism for transporting the optics/dispensng device in two dimensions, which X-Y drive mechanism has X and Y drive sources each including a motor and a corresponding power transmission sprocket for transmitting power from the motor to the optics/dispensing device. According to the invention, the shock absorbing apparatus comprises a slip clutch interposed between each drive motor and corresponding power transmission sprocket. The slip clutch comprises a clutch plate, a ball retaining plate, the power transmission sprocket, and a guide plate. The clutch plate is fixedly secured to a drive shaft protruding from a gear box which drives the sprocket, and the ball retaining plate, sprocket and guide plate are supported on the drive shaft for rotation. The drive shaft has a stopper affixed thereto for urging the ball retaining plate, sprocket and guide plate toward the clutch plate for operative association therewith.

Other features and advantages of the invention will be apparent from the following description taken in conjunction with the accompanying drawings in which like reference characters designate the same or similar parts through the figures thereof.

DETAILED DESCRIPTION OF THE PREFERRED EMBODIMENT

Figure 1:
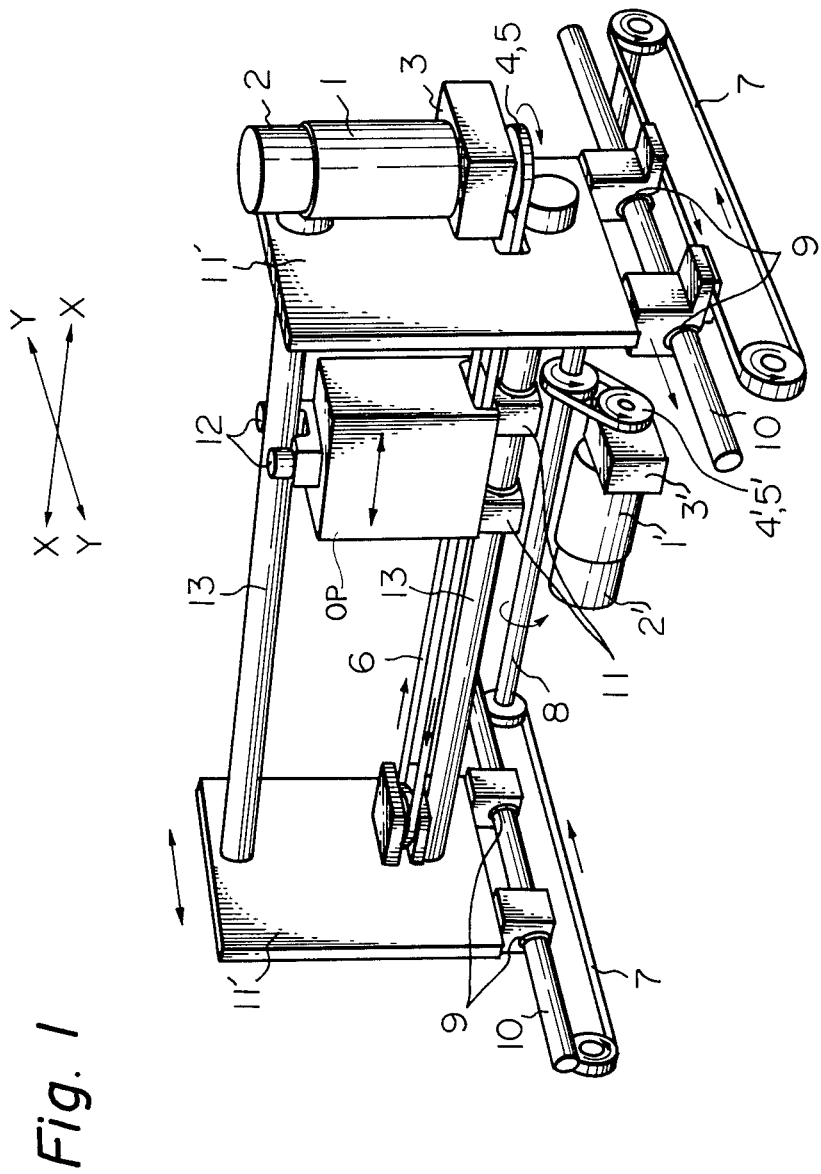
FIG. 1 is a perspective view illustrating an automatic analyzing and measuring apparatus incorporating a shock absorbing mechanism embodying the present invention.

Referring FIG. 1, an automatic analyzing and measuring apparatus includes drive motors 1, 1' constituting the sources of drive for the X and Y axes, respectively, encoder/decoders 2, 2' rotatively driven by the drive motors 1, 1', respectively, gear boxes 3, 3' driven by the drive motors 1, 1', sprockets 4, 4' driven by the motors 1, 1' via the respective gear boxes 3, 3', slip clutches 5, 5', a belt 6 associated with the sprocket 4 and slip clutch 5 for X-axis drive, a pair of belts 7 for Y-axis drive, a Y-direction drive shaft 8 for driving the belts 7, Y-axis guide shoes 9, a pair of Y-axis guide rails 10, X-axis guide shoes 11, X-axis guide rollers 12, and a pair of X-axis guide rails 13. The drive motors 1, 1' have respective rotary shafts which, in driving the gear boxes 3, 3', simultaneously rotate the corresponding encoder/decoders 2, 2' to control both travelling distance and travelling speed along the X and Y axes. OP denotes an optics/dispensing mechanism which, by way of example, may apply the surface of a reaction carrier with samples or reagents and then detect the optical response of the resulting reaction product. The gear boxes 3, 3' rotate the sprockets 4, 4' upon reducing the rotational speed of the drive motors 1, 1' by a prescribed gear ratio. In the event of a malfunction or the application of an excessive force, the slip clutches 5, 5', of which slip clutch 5 is shown in greater detail in FIG. 2, act as shock absorbing mechanisms to interrupt the transmission of rotational motion from the drive motors 1, 1' to the sprockets 4, 4' and to stop the motors, as will be described below.

The Y-axis drive shaft 8, rotated by the sprocket 4', drives the two belts 7, whereas the belt 6 is driven directly by the sprocket 4. The belts 7 are affixed to a portion of a Y-movement stage 11' so that the belts 7 and Y-movement stage 11' move in unison. The belt 6 is affixed to a portion of the optics/dispensing mechanism, described later, so that these may similar move in unison. The Y-movement stage 11' is transported in the Y-direction on the two guide rails 10, via the guide bushes 9, by means of the Y-axis drive source acting through the belts 7. The optics/dispensing mechanism OP, on the other hand, supported on the guide rails 13 via the guide bushes 11 and guide rollers 12, is moved in the X-direction by the X-axis drive source acting through the belt 6. Such an arrangement makes it possible to move, position and stop the optics/dispensing mechanism at any desired location located in the X-Y plane.

Figure 2:
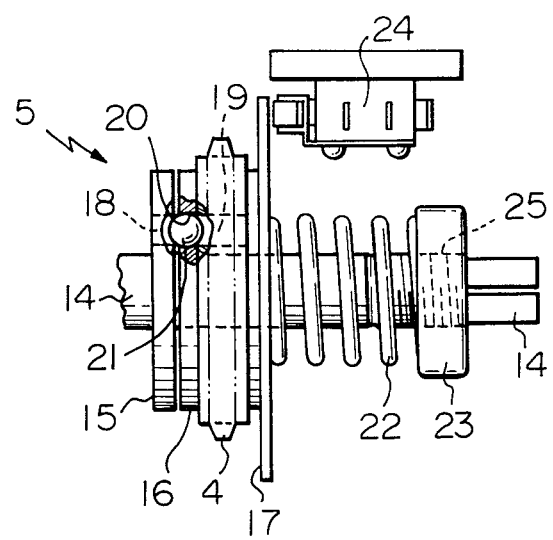
FIG. 2 is a side section, partially broken away, illustrating a slip clutch.

As shown in FIG. 2, a clutch plate 15, a ball retaining plate 16, the sprocket 4 and a guide plate 17 are disposed on a drive shaft 14 extending from the gear box for driving the sprocket 4. The clutch plate 15 is fixedly secured to the drive shaft 14, while the ball retaining plate 16, sprocket 4 and guide plate 17 are freely rotatable with respect to the drive shaft 14. Clutch plate 15 is provided with at least three holes 18 bored through the outer circumferential portion thereof, in alignment with at least three holes 19 similarly bored through the outer circumferential portion of the sprocket 4. The ball retaining plate 16 is provided with holes 20, each retaining a ball 21, at positions corresponding to the matched holes 18, 19. A spring 22 is compressed between the guide plate 17 and a stopper 23 which is threadedly affixed to the drive shaft 14, whereby the guide plate 17, sprocket 4 and balls 21 are pressed toward the clutch plate 15 to operate in association therewith. In the event of a malfunction, or if the sprocket 4 should happen to be subjected to an excessive force, the balls 21 retained by the plate 16 will slip out of the holes 18 or 19 and the guide plate 17 will be forced to the right in FIG. 2, causing the guide plate 17 to actuate a switch 24 that will in turn halt the drive motor 1. The force applied by the spring 22 may be adjusted by moving the stopper 23 to the left or right along a threaded portion 25 formed on the drive shaft 14 to which the stopper 23 is attached.

Since correct correlation between the read-out of the encoder/decoder 2 and the positions along the X and Y axes ordinarily will be lost when the switch 24 is actuated to stop the motor, it is essential that the initial conditions be restored once the balls 21 have been properly re-engaged with the holes 18, 19. To accomplish this, the Y-movement stage and the optics/dispensing mechanism OP are moved back to the origin of the X and Y axes, after which the encoder reading is reset.

It should be noted that the slip clutch arrangement of the slip clutch 5' is identical with that of the slip clutch 5 just described. A description of said arrangement is therefore omitted to avoid prolixity.

Incorporating the shock absorbing mechanism of the present invention in an automatic analyzing and measuring apparatus greatly enhances operating safety and assures that continuous analytical measurements will proceed with a high degree of reliability.

As many apparently widely different embodiments of the present invention may be made without departing from the spirit and scope thereof, it is to be understood that the invention is not limited to the specific embodiments thereof except as defined in the appended claims.

What is claimed is:

1. A shock absorbing mechanism in an automatic analyzing and measuring apparatus of the type having an optics/dispensing device and an X-Y drive mechanism for transporting the optics/dispensing device in two dimensions, which X-Y drive mechanism has X and Y bidirectional drive sources each including a reversible drive motor and a corresponding power transmission sprocket for transmitting power from the motor to the optics/dispensing device, said shock absorbing apparatus comprising a slip clutch interposed between each drive motor and corresponding power transmission sprocket, said slip clutch comprises balls, a clutch plate, a ball retaining plate, said power transmission sprocket, and a guide plate, said clutch plate being fixedly secured to a drive shaft, said ball retaining plate, sprocket and guide plate being supported on said drive shaft for rotation, said clutch plate provides holes bored through an outer circumferential portion thereof alignable with holes bored in said sprocket, said ball retaining plate being disposed between said clutch plate and said sprocket and being freely rotatable with respect thereto, said ball retaining plate providing holes each retaining a respective ball, said balls cooperating with said clutch plate holes and sprocket holes to transfer torque from said drive shaft to said sprocket, said ball retaining plate, sprocket and guide plate being axially displaceable along said drive shaft from said clutch plate, said drive shaft having a stopper affixed thereto and a spring being compressed between said guide plate and the stopper for urging said ball retaining plate, sprocket and guide plate toward said clutch plate for operative association therewith, whereby when said sprocket is subjected to an excessive force said balls slip out of one of said clutch plate holes and sprocket holes causing said guide plate to move axially away from said clutch plate against said spring and actuate a switch so as to halt said drive motor.

2. A shock absorbing mechanism according to claim 1, wherein said balls slip out of one of said clutch plate holes and sprocket holes when said sprocket is subjected to an excessive force regardless of said drive shaft rotational direction.

* * * * *